US006111143A

United States Patent [19]
Park et al.

[11] Patent Number: 6,111,143
[45] Date of Patent: *Aug. 29, 2000

[54] SULFONIUM SALT AND ITS MANUFACTURING METHOD

[75] Inventors: Joo-Hyeon Park; Dong-Chul Seo; Sun-Yi Park; Seong-Ju Kim, all of Taejeon, Rep. of Korea

[73] Assignee: Korea Kumbo Petrochemical Co., Ltd., Seoul, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 09/140,955

[22] Filed: Aug. 27, 1998

[30] Foreign Application Priority Data

Jul. 16, 1998 [KR] Rep. of Korea .................. 98-28833

[51] Int. Cl.$^7$ ............................................. C07C 315/00
[52] U.S. Cl. ........................... 568/35; 568/18; 568/29; 568/28
[58] Field of Search ............................ 568/18, 77, 74, 568/28, 29, 33, 34, 35, 36, 38, 43

[56] References Cited

U.S. PATENT DOCUMENTS

| | | | |
|---|---|---|---|
| 4,120,866 | 10/1978 | Winkler | 260/315 |
| 4,246,259 | 1/1981 | Kathawala | 568/18 |
| 4,786,441 | 11/1988 | Miller | 562/113 |
| 5,274,148 | 12/1993 | Dougherty et al. | 556/64 |
| 5,633,409 | 5/1997 | Watanabe | 568/49 |
| 5,705,702 | 1/1998 | Osawa | 568/77 |

FOREIGN PATENT DOCUMENTS

| | | | |
|---|---|---|---|
| 0327194 | 8/1989 | European Pat. Off. | C07C 149/46 |
| 0455083 | 11/1991 | European Pat. Off. | C07C 381/12 |
| 2644591 | 4/1978 | Germany . | |

OTHER PUBLICATIONS

"The Preparation of Triarylsulfonium Halides by the Action of Aryl Grignard Reagents on Diphenyl Sulfoxide," Bernard S. Wildi et al., pp. 1965–1967, vol. 73, May 1951.

"Photochemistry of Triarysulfonium Salts," John L. Dektar et al., pp. 6014–6015, J. Am. Chem. Soc., vol. 112, No. 16, 1990.

"Deoxygenation of Sulfoxides Promoted by Electrophilic Silicon Reagents: Preparation of Aryl–Substituted Sulfonium Salts," R.D. Miller et al., J. Org. Chem. 1988, 53, pp. 5571–5573.

CA:87:134348 abs of Chem Lett by Minato, (6) pp. 609–614, 1977.

Angewandte Chem International English addition vol. 19, No. 3 by Effenberger pp. 151–171, 1980.

Tetrahedron Letters No. 4 by Hendrickson pp. 277–280, 1975.

Chem. Pharm. Bull vol. 29 No. 12 by Endo pp. 3753–3755, 1981.

CA:119:180471 abs Res Disclos. by Anon 350, 390, 1993.
CA:120:232097 abs of JP05255240, 1992.
CA:113:58341 abs of J Am Chem Soc 112 (16) By Dektar pp. 6004–6015, 1990.
CA:115:193968 abs of Proc. SPIE–Int. Soc. Opt. Eng., 1466(Adv. Resist Technoll. process.8)by Schwartz et al pp. 26–38, 1991.

*Primary Examiner*—Jean F. Vollano
*Attorney, Agent, or Firm*—Davidson, Davidson & Kappel, LLC

[57] ABSTRACT

This invention relates to a sulfonium salt, including its manufacturing method, which is effectively used as a photoacid initiator or radical photoinitiator during polymerization and a photoacid generator, leaving the protection groups of organic compounds, especially as an useful photoacid generator of the chemically amplified photoresist employed in semiconductor materials. Since the sulfonium salt of this invention, so prepared via one-step reaction between sulfoxide compound and aromatic compound in the presence of perfluoroalkanesulfonic anhydride, has the advantages in that by overcoming some shortcomings of the prior art to prepare the sulfonium salt via two steps using Grinard reagent, this invention may provide a novel sulfonium salt with higher yield which cannot be achieved in the prior art and also to prepare even any conventional sulfonium salt having better yield.

2 Claims, No Drawings

SULFONIUM SALT AND ITS MANUFACTURING METHOD

BACKGROUND OF THE INVENTION

1. Field of the Invention

This invention relates to a sulfonium salt and its manufacturing method and more particularly, to the sulfonium salt, represented by the following formula I including its manufacturing method, which is effectively used as a photoacid initiator or radical photoinitiator during polymerization and a photoacid generator leaving the protection groups of organic compounds.

Formula I

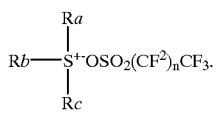

in which, Ra, Rb and Rc are independently alkyl group, aryl group, allyl group, aromatic compound or benzyl group, respectively; n is an integer of 0 to 20.

2. Discussion of Related Art

In general, sulfonium salt is being effectively used as a photoacid initiator or radical photoinitiator during polymerization and a photoacid generator leaving the protection groups of organic compounds. Further, the sulfonium salt has been recently spotlighted as a photoacid generator of the chemically amplified photoresist, being employed in semiconductor materials.

According to the conventional method, it has been disclosed that the sulfonium salt is synthesized via two-step reaction in the presence of Grignard reagent (J. Am. Chem. Soc., 1990, 112, 6004–6015). Nevertheless, the conventional method recognized some disadvantages in that excess of Grignard reagent should be inevitably added in the two-step reaction and the full-scale industrial production has proven to be unavailable due to poor yield of final product.

Under the consideration of such a technological problem, further research has focused on the method of synthesizing the sulfonium salt via one-step reaction in the presence of trialkylsilyl triflate (J. Org. Chem., 1988, 53, 5571–5573). However, such method has failed to improve the poor yield related problem.

SUMMARY OF THE INVENTION

Therefore, an object of this invention is to provide a novel sulfonium salts.

Another object of this invention is to provide a method of manufacturing sulfonium salt, wherein one-step reaction between sulfoxide compound and aromatic compound instead of Grignard reagent is performed in the presence of perfluoroalkanesulfonic anhydride, thus making it available to prepare a novel sulfonium salt with higher yield which cannot be achieved in the prior art and also to prepare even any conventional sulfonium salt having better yield.

To achieve the above objective, the sulfonium salt of this invention is characterized by the following formula I.

Formula I

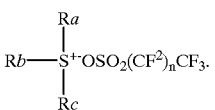

in which, Ra, Rb and Rc are independently alkyl group, aryl group, allyl group,

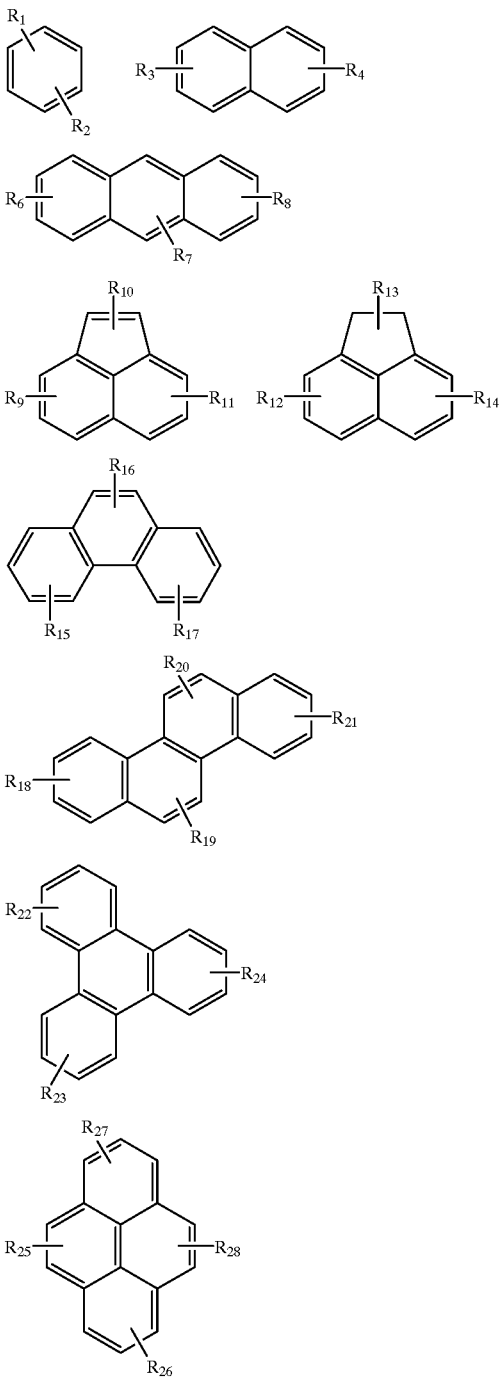

-continued

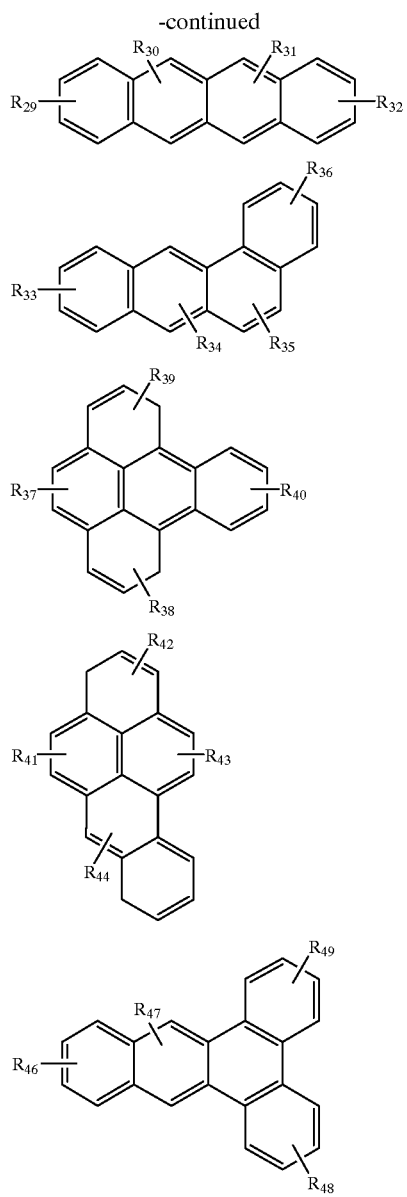

or benzyl group respectively;

$R_1$ to $R_{49}$ are independently hydrogen atom, alkyl group, vinyl group, allyl group, aryl group, benzyl group, hydroxy group, thiol group, halogen atom, ester group, aldehyde group, alkoxy group, thioalkoxy group, phenoxy goup, thiophenoxy group, or nitrile group;

n is an integer of 0 to 20.

Further, this invention is also characterized by providing a method of manufacturing the sulfonium salt represented by the formula I via reaction among sulfoxide compound expressed by the following formula II, an aromatic compound represented by the following formula III and perfluoroalkanesulfonic anhydride represented by the following formula IV.

Formula II

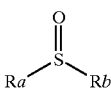

Where, Ra and Rb are the same as defined above.

Formula III

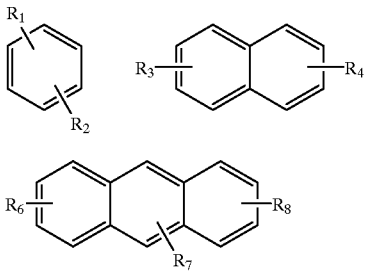

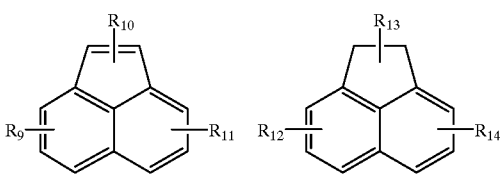

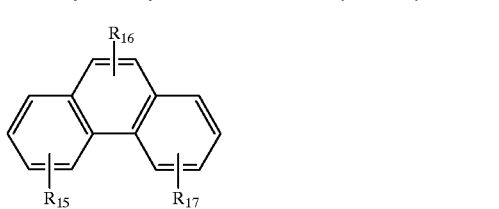

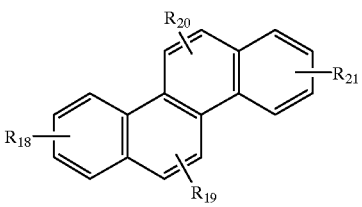

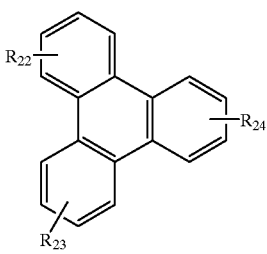

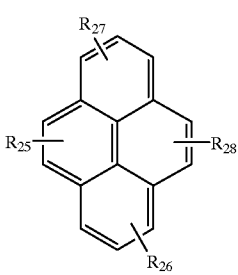

-continued

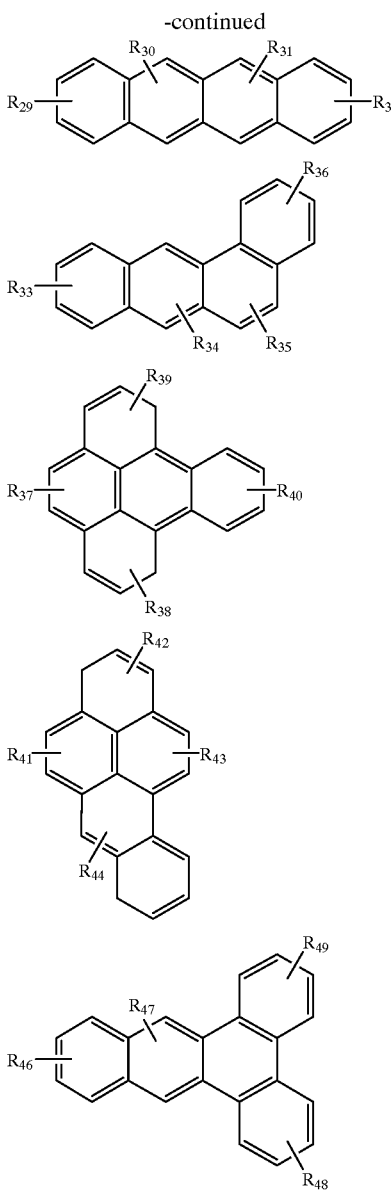

in which, $R_1$ to $R_{49}$ are the same as defined above.
Formula IV

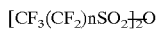

$[CF_3(CF_2)_nSO_2]_2O$ in which, n is the same as defined above.

DETAILED DESCRIPTION OF PREFERRED EMBODIMENT

This invention is explained in more detail as set forth hereunder.

The method of manufacturing the sulfonium salt according to this invention is based on one-step reaction in which both sulfoxide compound and aromatic compound dissolved in a solvent are stirred in the presence of perfluoroalkanesulfonic anhydride.

The method of manufacturing the sulfonium salt according to this invention is represented by the following reaction scheme.

Scheme 1

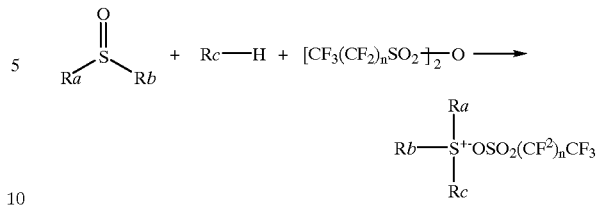

in which, Ra, Rb, Rc and n are the same as defined above.

As defined above, the sulfoxide compound of this invention, represented by the formula II, may include any one of common sulfoxide compounds selected from the group consisting of alkyl sulfoxide, aryl sulfoxide, alkylaryl sulfoxide, allyl sulfoxide, alkylallyl sulfoxide, and arylallyl sulfoxide.

Among the above compounds, however, the reactability of alkyl sulfoxide is slightly lower than that of aryl sulfoxide. Further, the sulfonium compound with higher yield may be obtained by those compounds regardless of functional groups present in sulfoxide compounds; examples of the functional groups include ester group, ether group, thioester group, sulfanyl group, alcohol group, amide group, ketone group, aldehyde group, and halogen group.

The aromatic compound represented by the formula III may contribute to higher yield of a desired product regardless of any functional groups. If there are any functional groups having excellent selective substitution power at the para-position, a lot of para-oriented products are obtained.

Meantime, if the reaction temperature is high, the selective substitution power at the para-position is slightly reduced. For example, when phenyl sulfoxide, toluene and trifluoromethanesulfonic anhydride are reacted at below 0° C., diphenyl(4-methylphenyl)sulfonium triflate having the selective substitution power at the para-position is only generated, while a small amount of diphenyl(2-methylphenyl)sulfonium triflate having the selective substitution power at the ortho-position is generated at more than room temperature.

The amount of aromatic compound represented by the formula III is in the range of 1 to 100 equivalents per equivalent of sulfoxide compound represented by the formula II, preferably in the range of 1 to 1.5 equivalents.

Meantime, perfluoroalkanesulfonic anhydride may include all of the common compounds and among them, the typical compound is trifluoromethanesulfonic anhydride.

The amount of perfluoroalkanesulfonic anhydride is in the range of 1 to 5 equivalents per equivalent of sulfoxide compound represented by the formula II, preferably in the range of 1 to 1.5 equivalents.

During the process of manufacturing the sulfonium salt using those compounds, examples of reaction solvent include dichloromethane, chloroform, carbon tetrachloride, acetonitrile, ethyl acetate, ethyl ether, and dioxane; among them, haloalkane compounds are rather appropriate, even if unspecified.

According to this invention, the aromatic compound represented by the formula III may be employed as a reacting solvent as well as a reactant in consequence. However, as a case demands, the non-use of such aromatic compound as solvent does not raise any problem.

In addition, the manufacture of sulfonium salt is performed at −80 to 100° C.; if the reaction in temperature is extremely high, the generation of byproducts may be responsible for poor yield. Occasionally, when the reaction temperature increases, a mixture of both para-oriented and ortho-oriented materials may be generated.

As for a method of manufacturing the sulfonium salt according to this invention unlike the prior arts, the final product may be synthesized using alkyl sulfoxide; further, the sulfonium salt substituted by halogen or ester group may be freely prepared. It is nearly impossible to prepare the sulfonium salt in the conventional method using Grignard reagent.

When the patterning of pattern in a photoresist composition derived from the sulfonium salt of this invention together with some basic resin and additives in small amounts are examined, better photoresist pattern is observed than the conventional sulfonium salt. As a matter of course, the sulfonium salt of this invention is effectively used as a photoacid initiator or radical photoinitiator during polymerization and a catalyst leaving the protection groups of organic compounds.

This invention is explained in more detail based on the following Examples but is not limited by those Examples. The sulfonium salts prepared by the following Examples are shown in the following table 1.

TABLE 1

| Exam | Formula | m.p., °C. | Exam | Formula | m.p., °C. |
|---|---|---|---|---|---|
| 2 | [structure with p-tolyl group] | 132–134 | 3 | [triphenylsulfonium triflate] | 101–102 |
| 4 | [structure with p-isobutylphenyl] | 100–101 | 5 | [structure with p-tert-butylphenyl] | 112–113 |
| 6 | [structure with p-methoxyphenyl] | 98–100 | 7 | [structure with p-phenoxyphenyl] | 89–91 |
| 8 | [structure with p-phenylthiophenyl, SPh] | 81–82 | 9 | [structure with p-fluorophenyl] | 117–118 |

TABLE 1-continued

| Exam | Formula | m.p., °C. | Exam | Formula | m.p., °C. |
|---|---|---|---|---|---|
| 10 | [Ph-S⁺-C₆H₄-Cl]₂ ⁻OSO₂CF₃ | 111–112 | 11 | [Ph-S⁺-C₆H₄-Br]₂ ⁻OSO₂CF₃ | 111–112 |
| 12 | [Ph-S⁺-C₆H₄-CH₃]₂ ⁻OSO₂CF₃ | 151–152 | 13 | [Ph-S⁺-C₆H₄-O-CH₂-C(O)O-tBu]₂ ⁻OSO₂CF₃ | 91–92 |
| 14 | [Ph-S⁺-(1-naphthyl)]₂ ⁻OSO₂CF₃ | 132–133 | 15 | [Ph-S⁺-(4-(O-CH₂-C(O)O-tBu)-1-naphthyl)]₂ ⁻OSO₂CF₃ | 145–146 |
| 16 | [Ph-S⁺-(pyrenyl)]₂ ⁻OSO₂CF₃ | | 17 | [nBu]₂-S⁺-(1-naphthyl) ⁻OSO₂CF₃ | 103–104 |
| 18 | [Ph-S⁺-CH₂-Ph]₂ ⁻OSO₂CF₃ | 94–95 | 19 | Ph-S⁺(CH₃)-C₆H₄-S-CH₃ ⁻OSO₂CF₃ | 76–77 |

TABLE 1-continued

| Exam | Formula | m.p., °C. | Exam | Formula | m.p., °C. |
|---|---|---|---|---|---|
| 20 | [Ph-S⁺-OSO₂CF₃]₂ with phenanthrene | | 21 | [Ph-S⁺-OSO₂CF₃]₂ with methylphenyl-O-CH₂-C(O)-O-tBu | |
| 22 | [Ph-S⁺-OSO₂CF₃]₂ with phenyl-S-CH₂-C(O)-O-tBu | | 23 | (CH₃)₂-S⁺-OSO₂CF₃ with phenyl-O-CH₂-C(O)-O-tBu | |

EXAMPLE 1

Preparation of Diphenyl(Methyl Phenyl)Sulfonium Triflate 1 g of phenyl sulfoxide dissolved in 50 mL toluene was stirred at room temperature with a slow addition of 1.48 g of triflic anhydride and further stirred for 1 hour.

Then, the sulfonium salt contained in the reacting mixture was extracted with distilled water and further, toluene used as a solvent and reactant was removed. The sulfonium salt, so extracted with distilled water, was re-extracted with dichloromethane into organic layer and then, the extraction solvent dichloromethane was removed under pressure. After the solvent was completely removed, an oil phase with larger viscosity was obtained. The oil phase, so formed, was completely dissolved in dichloromethane and with a slow addition of ether, a white precipitate was obtained.

As a final step, the white precipitate was filtered, and dried by vaccum oven to obtain 2.06 g of the sulfonium salt in a white solid (yield: 96%).

As a result of analyzing the mixture, so formed, on $^1$H-NMR and $C^{13}$-NMR, it was understood that the mixture did contain both diphenyl(2-methyl phenyl)sulfonium triflate and diphenyl(4-methylphenyl)sulfonium triflate in a ratio of 18:82.

EXAMPLE 2

Preparation of Diphenyl(4-Methyl Phenyl) Sulfonium Triflate

Both 1 g of phenyl sulfoxide and 0.51 g of toluene dissolved in 50 mL dichloromethane was stirred and then, 1.48 g of triflic anhydride was slowly added to the mixture. The reacting mixture was stirred at the same temperature for 30 minutes, and the reaction temperature was slowly increased up to room temperature. Then, the reacting mixture was washed with distilled water. After the complete removal of organic solvent contained in the washed organic layer under vacuum drying, an oil phase with larger viscosity was obtained. The oil phase, so formed, was completely dissolved in dichloromethane and with a slow addition of ether, a white precipitate was obtained. The precipitate was filtered, and dried by vaccum oven to obtain 2.01 g of diphenyl(4-methyl phenyl)sulfonium triflate (yield: 94%) in a white solid. The formula was shown in the table 1.

EXAMPLE 3

Preparation of Triphenylsulfonium Triflate

In the procedure as described in Example 2, the sulfonium salt was prepared except that instead of using 0.51 g of toluene, 0.43 g of benzene was employed to obtain 1.89 g of triphenylsulfonium trilflate (yield: 96%). The formula was shown in the table 1.

EXAMPLE 4

Preparation of Diphenyl(4-Isobutyl Phenyl) Sulfonium Triflate

In the procedure as described in Example 2, the sulfonium salt was prepared except that instead of using 0.51 g of toluene, 0.74 g of isobutyl benzene was employed to obtain 2.13 g of diphenyl(4-isobutyl phenyl)sulfonium triflate (yield: 91%). The formula was shown in the table 1.

EXAMPLE 5

Preparation of Diphenyl(4-Tert-Butylphenyl) Sulfonium Triflate

In the procedure as described in Example 2, the sulfonium salt was prepared except that instead of using 0.51 g of toluene, 0.74 g of tert-butylbenzene was employed to obtain 2.25 g of diphenyl(4-tert-butylphenyl)sulfonium triflate (yield: 96%). The formula was shown in the table 1.

EXAMPLE 6

Preparation of Diphenyl(4-Methoxy Phenyl) Sulfonium Triflate

In the procedure as described in Example 2, the sulfonium salt was prepared except that instead of using 0.51 g of toluene, 0.59 g of anisole was employed to obtain 1.19 g of diphenyl(4-methoxy phenyl)sulfonium triflate (yield: 90%). The formula was shown in the table 1.

EXAMPLE 7

Preparation of Diphenyl(4-Phenoxy Phenyl) Sulfonium Triflate

In the procedure as described in Example 2, the sulfonium salt was prepared except that instead of using 0.51 g of toluene, 0.94 g of phenyl ether was employed to obtain 2.37 g of diphenyl(4-phenoxy phenyl)sulfonium triflate (yield: 94%). The formula was shown in the table 1.

EXAMPLE 8

Preparation of Diphenyl(4-Phenylsulfanyl Phenyl) Sulfonium Triflate

In the procedure as described in Example 2, the sulfonium salt was prepared except that instead of using 0.51 g of toluene, 1.02 g of phenylsulfide was employed to obtain 2.53 g of diphenyl(4-phenylsulfanyl phenyl)sulfonium triflate (yield: 97%). The formula was shown in the table 1.

EXAMPLE 9

Preparation of Diphenyl(4-Fluorophenyl)Sulfonium Triflate

In the procedure as described in Example 2, the sulfonium salt was prepared except that instead of using 0.51 g of toluene, 0.53 g of fluorobenzene was employed to obtain 1.85 g of diphenyl(4-fluorophenyl)sulfonium triflate (yield: 86%). The formula was shown in the table 1.

EXAMPLE 10

Preparation of Diphenyl(4-Chlorophenyl)Sulfonium Triflate

In the procedure as described in Example 2, the sulfonium salt was prepared except that instead of using 0.51 g of toluene, 0.62 g of chlorobenzene was employed to obtain 2.03 g of diphenyl(4-chlorophenyl)sulfonium triflate (yield: 93%). The formula was shown in the table 1.

EXAMPLE 11

Preparation of Diphenyl(4-Bromophenyl)Sulfonium Triflate

In the procedure as described in Example 2, the sulfonium salt was prepared except that instead of using 0.51 g of toluene, 0.86 g of bromobenzene was employed to obtain 2.40 g of diphenyl(4-bromophenyl)sulfonium triflate (yield: 98%). The formula was shown in the table 1.

EXAMPLE 12

Preparation of Diphenyl(4-Iodophenyl)Sulfonium Triflate

In the procedure as described in Example 2, the sulfonium salt was prepared except that instead of using 0.51 g of toluene, 1.12 g of iodobenzene was employed to obtain 2.21 g of diphenyl(4-iodophenyl)sulfonium triflate (yield: 82%). The formula was shown in the table 1.

EXAMPLE 13

Preparation of Diphenyl(4-Tert-Butoxy Carbomethoxy Phenyl)Sulfonium Triflate

In the procedure as described in Example 2, the sulfonium salt was prepared except that instead of using 0.51 g of toluene, 1.15 g of tert-butyl phenoxyacetate was employed to obtain 2.36 g of diphenyl(4-tert-butoxycarbomethoxyphenyl)sulfonium triflate (yield: 87%). The formula was shown in the table 1.

EXAMPLE 14

Preparation of Diphenyl(Naphthalen-1-yl)Sulfonium Triflate

In the procedure as described in Example 2, the sulfonium salt was prepared except that instead of using 0.51 g of toluene, 0.70 g of naphthalene was employed to obtain 2.29 g of diphenyl(naphthalen-1-yl)sulfonium triflate (yield: 99%). The formula was shown in the table 1.

EXAMPLE 15

Preparation of Diphenyl(4-Tert-Butoxy Carbomethoxy Naphthalen-1-yl)Sulfonium Triflate In the procedure as described in Example 2, the sulfonium salt was prepared except that instead of using 0.51 g of toluene, 1.42 g of tert-butyl 1-naphtyloxyacetate was employed to obtain 2.40 g of diphenyl(4-tert-butoxy carbomethoxy naphthalen-1-yl)sulfonium triflate (yield: 81%). The formula was shown in the table 1.

EXAMPLE 16

Preparation of Diphenyl(Pyrenyl)Sulfonium Triflate

In the procedure as described in Example 2, the sulfonium salt was prepared except that instead of using 0.51 g of toluene, 1.11 g of pyrene was employed to obtain 1.37 g of diphenyl(pyrenyl)sulfonium triflate (yield: 51%). The formula was shown in the table 1.

EXAMPLE 17

Preparation of Dibutyl(Naphthalen-1-yl)Sulfonium Triflate

In the procedure as described in Example 2, the sulfonium salt was prepared except that instead of using 0.51 g of toluene and 1 g of phenyl sulfoxide, 0.70 g of naphthalene and 0.81 g of butyl sulfoxide, respectively, were employed to obtain 1.65 g of dibutyl(naphthalen-1-yl)sulfonium triflate (yield: 78%). The formula was shown in the table 1.

EXAMPLE 18

Preparation of Diphenyl(Benzyl)Sulfonium Triflate

In the procedure as described in Example 2, the sulfonium salt was prepared except that instead of using 0.51 g of toluene and 1 g of phenyl sulfoxide, 0.43 g of benzene and 1.08 g of benzylphenyl sulfoxide, respectively, were employed to obtain 1.83 g of dibutyl(benzyl)sulfonium triflate (yield: 86%). The formula was shown in the table 1.

EXAMPLE 19

Preparation of Methyl(Phenyl)(4-Methylsulfanyl Phenyl)Sulfonium Triflate

In the procedure as described in Example 2, the sulfonium salt was prepared except that instead of using 0.51 g of toluene and 1 g of phenyl sulfoxide, 0.68 g of thioanisole and 0.70 g of methylphenyl sulfoxide, respectively, were employed to obtain 1.56 g of methyl(phenyl)(4- methylsulfanyl phenyl)sulfonium triflate (yield: 79%). The formula was shown in the table 1.

EXAMPLE 20

Preparation of Diphenyl(Phenanthrenyl)Sulfonium Triflate

In the procedure as described in Example 2, the sulfonium salt was. prepared except that instead of using 0.51 g of toluene, 0.98 g of phenanthrene was employed to obtain 1.66 g of diphenyl(phenanthrenyl)sulfonium triflate (yield: 65%). The formula was shown in the table 1.

EXAMPLE 21

Preparation of Diphenyl(4-Tert-Butoxycarbomethoxy-3-Methyl Phenyl)Sulfonium Triflate In the procedure as described in Example 2, the sulfonium salt was prepared except that instead of using 0.51 g of toluene, 1.22 g of tert-butyl 2-tolyloxyacetate was employed to obtain 2.34 g of diphenyl(4-tert-butoxycarbomethoxy-3-methylphenyl)sulfonium triflate in oil phase (yield: 84%). The formula was shown in the table 1.

EXAMPLE 22

Preparation of Diphenyl(4-Tert-Butoxycarbothiomethoxy Phenyl)Sulfonium Triflate

In the procedure as described in Example 2, the sulfonium salt was prepared except that instead of using 0.51 g of toluene, 1.23 g of tert-butyl phenylsulfanylacetate was employed to obtain 2.29 g of diphenyl(4-tert-butoxycarbothiomethoxy phenyl)sulfonium triflate in oil phase (yield: 82%). The formula was shown in the table 1.

EXAMPLE 23

Preparation of Dimethyl(Tert-Butoxycarbomethoxy Phenyl)Sulfonium Triflate

In the procedure as described in Example 2, the sulfonium salt was prepared except that instead of using 0.51 g of toluene and 1 g of phenyl sulfoxide, 1.15 g of tert-butyl phenoxyacetate and 0.39 g of methyl sulfoxide was employed to obtain 1.48 g of dimethyl(tert-butoxycarbomethoxyphenyl)sulfonium triflate in oil phase (yield: 72%). The formula was shown in the table 1.

COMPARATIVE EXAMPLE 1

Preparation of Triphenyl Sulfonium Triflate
I) Preparation of triphenyl sulfonium triflate
Phenyl magnesium bromide derived from 47 g of bromobenzene and 7 g of magnesium was prepared in the presence of absolute ether. After the removal of ether, a mixture of 50 mL benzene and 100 mL heptane was added to a reactor and then, the reaction temperature was increased up to 80° C. 12.1 g of diphenyl sulfoxide was dissolved in 75 mL benzene and then, this solution was slowly added to a solution containing phenyl magnesium bromide. Hence, the temperature of reacting solution was kept at 8° C. and after the addition was completed, the reacting mixture was stirred at the same temperature for 3 hours and cooled to room temperature. With a slow addition of 200 mL of 25% HBr aqueous solution, the aqueous solution layer was separated, while an organic layer was extracted two times using 30 mL of 5% HBr aqueous solution. After the collection of the aqueous solution, so extracted, the solution was further extracted with 250 mL dichloromethane. The dichloromethane layer, so extracted, was dried over anhydrous magnesium sulfate and then, the solvent was evaporated under vacuum drying. The remaining compound in oil phase was recrystallized using dichloromethane and ether, and dried to obtain 10.8 g of triphenyl sulfonium triflate (yield: 52%).

II) Preparation of triphenyl sulfonium triflate 25.6 g of triphenyl sulfonium triflate, so obtained from the above I), was dissolved in 200 mL dichloromethane and added to 6.8 mL triflic acid. The reacting solution was heated for 2 hours and after removal of HBr, a byproduct, was cooled to room temperature. The solution was washed with an aqueous solution of NaHCO$_3$ saturated with 50 mL water. After the organic layer was separated, the solution was dried over anhydrous magnesium sulfate and then, dichloromethane was removed. Hence, a solid compound, so formed, was recrystallized with ethylacetate to obtain 25.6 g of triphenyl sulfonium triflate (yield: 83%).

COMPARATIVE EXAMPLE 2

Preparation of Triphenyl Sulfonium Triflate 2.0 g of phenyl sulfoxide dissolved in 20 mL dichloromethane was cooled to −78° C. and then, 2.3 mL trimethylsilyl triflate was slowly added to the mixture for more than 5 minutes. The reacting mixture was stirred at the same temperature for 10 minutes and with the gradual increase of reaction temperature, stirred at 0° C. for 30 minutes. The solution was again cooled to −78° C. and 10 mL tetrahydrofuran solution of 2.0 M phenyl magnesium bromide was slowly added to the reacting solution. The reacting mixture was stirred at the same temperature for 30 minutes and further stirred at 0° C. for 30 minutes. The reaction was completed in 30 mL of 3% triflic acid aqueous solution. The reactant was diluted with 200 mL ether and extracted two times with 30 mL of triflic acid aqueous solution. The aqueous solution, so extracted, was further extracted three times with 30 mL chloroform. After collection of the organic layer, the solution was dried over anhydrous Na$_2$SO$_4$ and filtrated to remove the solvent. Thus, 1.9 g of triphenyl sulfonium triflate (yield: 50%) was obtained as a white solid.

As described above in more detail, the sulfonium salt of this invention, so prepared via one-step reaction between sulfoxide compound and aromatic compound in the presence of perfluoroalkanesulfonic anhydride, has the following advantages in that a) by overcoming some shortcomings of the prior art to prepare the sulfonium salt via two steps using Grinard reagent, this invention may provide a novel sulfonium salt with higher yield which cannot be achieved in the prior art and also to prepare even any conventional sulfonium salt having better yield, and b) the sulfonium salt of this invention may be effectively used as a photoacid initiator or radical photoinitiator during polymerization and a photoacid generator leaving the protection groups of organic compounds, especially as an useful photoacid generator of the chemically amplified photoresist employed in semiconductor materials.

What is claimed is:

1. A method of manufacturing the sulfonium salt represented by the following formula I

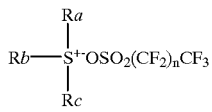
(I)

wherein Ra, Rb, and Rc are independently an alkyl group, aryl group, allyl group or benzyl group, and n is an integer of 0 to 20, which comprises:

preparing the sulfonium salt in a one-step reaction by stirring at a temperature in the range of −80 to 100° C., in the presence of perfluoroalkane sulfonic anhydride as defined below, a sulfoxide compound as defined below and an aromatic compound as defined below, said sulfoxide compound and said aromatic compound being dissolved in an organic solvent, said sulfoxide compound being represented by the following formula II

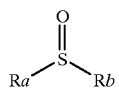
(II)

wherein Ra, Rb, and Rc are the same as defined above, said aromatic compound being represented by the following formula III

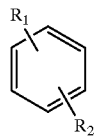 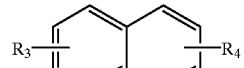
(III)

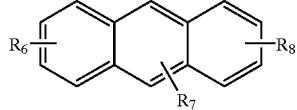

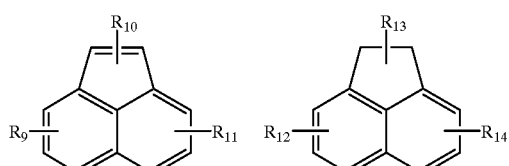

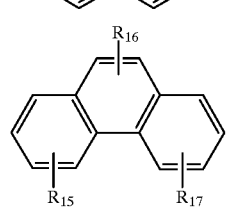

-continued

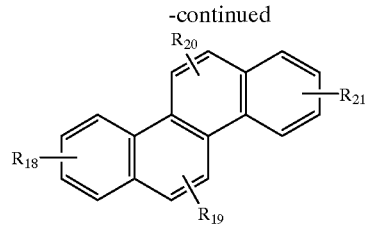

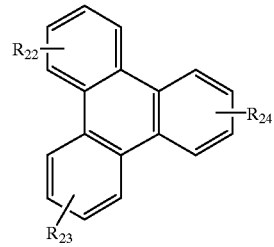

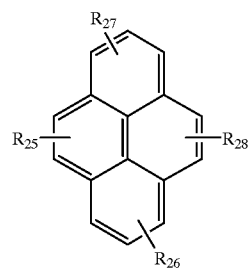

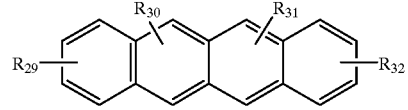

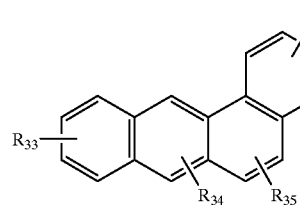

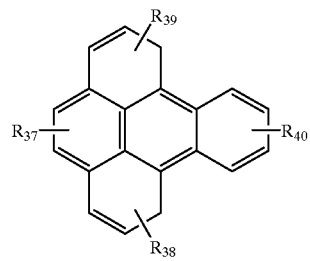

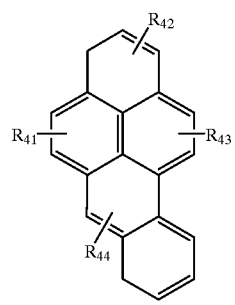

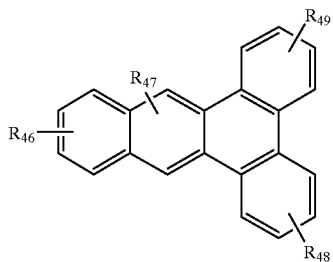

wherein $R_1$ to $R_{49}$ are independently hydrogen atom, alkyl group, vinyl group, allyl group, aryl group, benzyl group, hydroxy group, thiol group, halogen atom, ester group, aldehyde group, alkoxy group, thioalkoxy group, phenoxy group, thiophenoxy group, or nitrile group, wherein the amount of said aromatic compound is in the range of 1 to 100 equivalents to said sulfoxide compound, said perfluoroalkanesulfonic anhydride being represented by the following formula IV $$[CF_3(CF_2)_nSO_2]_2O \tag{IV}$$

wherein n is the same as defined above, and wherein the amount of said perfluoroalkanesulfonic anhydride is in the range of 1 to 5 equivalents to said sulfoxide compound.

2. The method of claim 1, wherein the organic solvent is selected from the group consisting of haloalkane, haloalkene, ester, ether, alkane, alkene, aromatic compounds, amides and nitrites.

* * * * *